(12) United States Patent
Aulbach et al.

(10) Patent No.: US 6,262,197 B1
(45) Date of Patent: *Jul. 17, 2001

(54) MULTINUCLEAR METALLOCENE COMPOUND, A PROCESS FOR ITS PREPARATION AND ITS USE AS CATALYST

(75) Inventors: Michael Aulbach, Hofheim; Michael-Joachim Brekner, Eschborn; Frank Küber, Oberursel; Roland Zenk, Bad Soden, all of (DE)

(73) Assignee: Targor GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/635,408

(22) Filed: Apr. 26, 1996

(30) Foreign Application Priority Data

Apr. 27, 1995 (DE) .............................. 195 14 301
Jun. 6, 1995 (DE) .............................. 195 20 599

(51) Int. Cl.⁷ .................. C08F 4/64; C08F 4/68; C08F 4/69; C07F 17/00
(52) U.S. Cl. .................. 526/127; 526/160; 526/943; 502/103; 502/117; 502/152; 502/154; 556/11; 556/43; 556/52; 556/53; 556/58; 556/87
(58) Field of Search ............... 556/52, 53, 11, 556/43, 58, 87; 502/117, 152, 154; 526/127, 160, 943

(56) References Cited

U.S. PATENT DOCUMENTS

| 4,769,510 | 9/1988 | Kaminsky et al. . |
| 5,243,001 | 9/1993 | Winter et al. . |
| 5,278,264 | 1/1994 | Spaleck et al. . |
| 5,328,969 | 7/1994 | Winter et al. . |
| 5,359,102 | * 10/1994 | Inoue et al. ................ 556/53 |
| 5,372,980 | 12/1994 | Davis . |
| 5,455,366 | 10/1995 | Rohrmann et al. . |
| 5,585,508 | * 12/1996 | Kuber et al. ................ 556/11 |
| 5,892,079 | * 4/1999 | Wilson, Jr. ................ 556/11 |

FOREIGN PATENT DOCUMENTS

| 2095100 | 10/1993 | (CA) . |
| 2099214 | 12/1993 | (CA) . |
| 0 528 041 | 2/1993 | (EP) . |
| 0528041A1 | * 2/1993 | (EP) . |
| 0 654 476 | 5/1995 | (EP) . |
| 0654476A1 | * 5/1995 | (EP) . |

OTHER PUBLICATIONS

Ewen et al., "Crystal Structures and Stereospecific Propylene Polmerizations with chiral Hafnium Metallocene Catalysts" J. Am. Chem. Soc. 109, pp. 6544–6545 (1987).

* cited by examiner

Primary Examiner—David W. Wu
Assistant Examiner—R. Rabago
(74) Attorney, Agent, or Firm—Connolly Bove Lodge & Hutz LLP

(57) ABSTRACT

The present invention relates to a metallocene compound containing at least two metallocene fragments L—MX$_2$—L which are different from one another and having the formula I

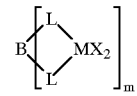

(I)

where B is a bridging unit, m is an integer from 2 to 100,000, M is a metal atom of group IVb, Vb or VIb of the Periodic Table of the Elements, X are identical or different in one metallocene fragment L—MX$_2$—L and are each, independently of one another, hydrogen, a $C_1$–$C_{40}$-hydrocarbon-containing group, an OH group, a halogen atom or a pseudohalogen, L are identical or different in one metallocene fragment and are each, independently of one another, a π ligand or another electron donor. The metallocene compound can advantageously be used as a catalyst component for olefin polymerization.

12 Claims, No Drawings

MULTINUCLEAR METALLOCENE COMPOUND, A PROCESS FOR ITS PREPARATION AND ITS USE AS CATALYST

The present invention relates to a multinuclear metallocene compound which is suitable as a catalyst component in the preparation of polyolefins. The invention also relates to a process for preparing these metallocenes. In addition, the invention relates to a process for preparing polyolefins using the metallocene compound of the invention.

Known from the literature is the preparation of polyolefins using soluble metallocene compounds in combination with aluminoxanes or other cocatalysts which, owing to their Lewis acidity, can convert the neutral metallocene into a cation and stabilize it.

Soluble metallocene compounds based on bis(cyclopentadienyl)zirconium dialkyl or dihalide in combination with oligomeric aluminoxanes can polymerize ethylene with good activity and propylene with moderate activity. The polyethylene obtained has a narrow molecular weight distribution and an intermediate molecular weight. The polypropylene prepared in this way is generally atactic and has a relatively low molecular weight.

The preparation of isotactic polypropylene is achieved by means of ethylenebis(4,5,6,7-tetrahydro-1-indenyl) zirconium dichloride together with an aluminoxane in a suspension polymerization (EP 185 918). The polymer has a narrow molecular weight distribution. The disadvantage of this process is that at polymerization temperatures relevant in industry only polymers having a very low molecular weight can be prepared.

Also known are catalysts based on ethylenebisindenylhafnium dichloride and ethylenebis(4,5,6,7-tetrahydro-1-indenyl)hafnium dichloride and methylaluminoxane using which relatively high molecular weight polypropylenes can be prepared by suspension polymerization (J. Am. Chem. Soc. (1987), 109, 6544). However, under polymerization conditions relevant in industry, the particle morphology of the polymers produced in this way is unsatisfactory and the activity of the catalyst systems used is comparatively low. In addition, these systems have high catalyst costs, so that low-cost polymerization is not possible using these systems.

A significant increase in the molecular weight was able to be achieved by using metallocenes in which the indenyl ligands fixed by means of a bridge bear substituents in the 2 position (EP 485 822) or in the 2 and 4 positions (EP 530 647).

A further increase in the molecular weight has been achieved by the use of indenyl ligands having substituents in the 2, 4 and 6 positions (BP 545 303) or of aromatic π ligands of the 4,5-benzoindenyl type (EP 549 900).

A disadvantage in the case of the stereospecific polymerization of prochiral monomers, e.g. of propylene, using metallocene catalysts is the relatively low isotacticity which in the case of isotactic polypropylene results in low melting points. Metallocenes having substituents in the 2 and 4 positions in particular and specifically rac-dimethylsilylbis(2-methyl-4-isopropylindenyl)zirconium dichloride in combination with methylaluminoxane give, in the case of propylene, a polymer having high isotacticity and therefore a high melting point (EP 530 647). A further increase in the melting point has been achieved by the use of 4-aryl-substituted bisindenyl systems (EP 576 970).

However, there are industrial applications in which low melting points are desired.

A disadvantage with the use of soluble (homogeneous) metallocene-methylaluminoxane catalyst systems in processes in which the polymer formed is obtained as a solid is the formation of heavy deposits on reactor walls and stirrer. These deposits are formed by agglomeration of the polymer particles if the metallocene or aluminoxane or both are present in dissolved form in the suspension medium. Such deposits in the reactor systems have to be regularly removed since they rapidly reach considerable thicknesses, have a high strength and prevent heat exchange to the cooling medium.

To avoid reactor deposits, metallocenes can be supported. Processes for this purpose are known (EP 578 838). For technical reasons, it would be advantageous to omit the additional process step of application to a support. EP 528 041 discloses binuclear metallocenes which are suitable for preparing syndiotactic polymers having a low molecular weight.

In many publications concerning metallocenes it is stated that metallocene mixtures are also suitable for the polymerization of olefins. However, the use of supported metallocene mixtures results in the following difficulties:

a) If mixtures of supported metallocenes are used, i.e. there is only one type of metallocene on each support particle, nonuniform particle size distributions are obtained in the reactor, which adversely affects the polymerization and the subsequent work-up of the polymerization products in respect of the throughput and the susceptibility to faults (e.g. limitation of the solids content in the polymerization in a liquid medium; instability of the fluidized bed in gas-phase processes; deposit formation; nonuniform particle separation in cyclones). In addition, the polymerization product obtained is a mixture of particles which each consist of a uniform polymer, so that the mixture has to be homogenized in the melt in a further extrusion step. Such a homogenization is increasingly incomplete with increasing difference between the polymers of the individual particles (e.g. molecular weight, viscosity) and increasing granulation throughput. Inhomogeneities in the corresponding polyolefins are the result.

b) If metallocene mixtures are supported as such, i.e. there are at least two different types of metallocene on each support particle, there is the problem of setting a particular composition of the mixture, since the composition of the mixture of the metallocenes fixed on the support changes as a function of the method of application to the support and the conditions of application to the support.

It is therefore an object of the invention to find a catalyst system which overcomes the disadvantages of the prior art.

It has surprisingly been found that this object is achieved by multinuclear metallocene compounds containing at least two metallocene fragments which are different from one another.

The present invention accordingly provides a multinuclear metallocene compound containing at least two metallocene fragments L—MX$_2$—L which are different from one another and having the formula I

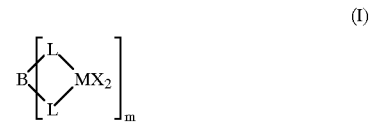

where B is a bridging unit, m is an integer from 2 to 100,000, preferably from 2 to 10, M is a metal atom of group IVb, Vb or VIb of the Periodic Table of the Elements, X are identical or different in one metallocene fragment L—MX$_2$—L and are each, independently of one another, hydrogen, a $C_1$–$C_{40}$- hydrocarbon-containing group, an OH group, a halogen atom or a pseudohalogen, L are identical or different in one metallocene fragment L—MX$_2$—L and are each, independently of one another, a π ligand or another electron donor.

The m metallocene fragments L—MX$_2$—L are different from one another or identical, with at least two of the m metallocene fragments L—MX$_2$—L being different from one another. Two metallocene fragments L—MX$_2$—L can be different from one another in one or more of the structural elements L, M and X.

Examples of M are titanium, zirconium, hafnium, vanadium, niobium, tantalum, chromium, molybdenum or tungsten. Preference is given to metallocenes of group IVb of the Periodic Table of the Elements, for example zirconium, hafnium and titanium.

The radicals X are each a hydrogen atom, a $C_1$–$C_{40}$-hydrocarbon-containing group such as a $C_1$–$C_{10}$-, preferably $C_1$–$C_4$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{12}$-arylalkyl group, a $C_7$–$C_{40}$-, preferably $C_7$–$C_{12}$-alkylaryl group, a $C_8$–$C_{40}$-, preferably $C_8$–$C_{12}$-arylalkenyl group, an OH group, a halogen atom such as fluorine, chlorine, bromine or iodine, preferably chlorine, or a pseudohalogen such as nitrile.

The ligands L are preferably each a π ligand such as a substituted or unsubstituted cyclopentadienylidene group or an electron donor such as O, S, PR$^4$ or NR$^4$, where R$^4$ is a hydrogen atom or a $C_1$–$C_{30}$-hydrocarbon radical such as $C_1$–$C_{20}$-alkyl or $C_6$–$C_{14}$-aryl Examples of L are:
tert-butylamido, cyclohexylamido, phenylamido, 2,6-diisopropylphenylamido, 2,6-di-tert-butylphenylamido, cyclododecylamido, cyclopentadienylidene, or substituted cyclopentadienylidene groups such as tetramethylcyclopentadienylidene, methylcyclopentadienylidene, methyl-tert-butylcyclopentadienylidene, tert-butylcyclopentadienylidene, isopropylcyclopentadienylidene, dimethylcyclopentadienylidene, trimethylcyclopentadienylidene, trimethylethylcyclopentadienylidene, phenylcyclopentadienylidene, diphenylcyclopentadienylidene, indenylidene, 2-methylindenylidene, 2-ethylindenylidene, 3-methylindenylidene, 3-tert-butylindenylidene, 3-trimethylsilylindenylidene, 2-methyl-4-phenylindenylidene, 2-ethyl-4-phenylindenylidene, 2-methyl-4-naphthylindenylidene, 2-methyl-4-isopropylindenylidene, 4,5-banzoindenylidene, 2-methyl-4,5-benzoindenylidene, 2-methyl-α-acenaphthylindenylidene, 2-methyl-4,6-diisopropylindenylidene, fluorenylidene, 4-methylfluorenylidene or 2,7-di-tert-butylfluorenylidene.

For m=2, B is preferably

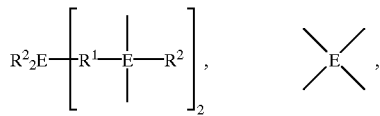

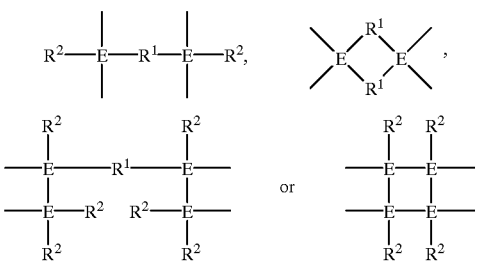

where the radicals R$^1$ are identical or different and are each a divalent $C_1$–$C_{40}$-hydrocarbon-containing bridging unit which can also contain one or more heteroatoms such as O, B, Si, Ge, N, P or B, the radicals R$^2$ are identical or different and are each a hydrogen atom, a halogen atom or a $C_1$–$C_{40}$-hydrocarbon-containing radical, and E are identical or different and are each, independently of one another, a carbon, silicon, germanium or tin atom.

Preferably, B is

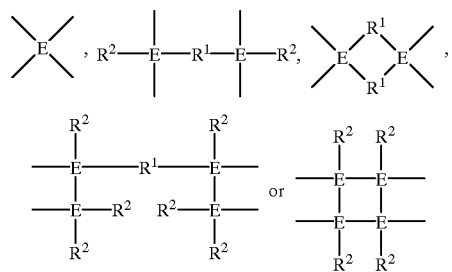

where the radicals R$^1$ are identical or different and are each a divalent $C_1$–$C_{40}$-alkanediyl, $C_1$–$C_{10}$-fluoroalkanediyl, $C_6$–$C_{10}$-arylene, $C_6$–$C_{10}$-fluoroarylene, $C_7$–$C_{20}$-alkylarylene, $C_7$–$C_{20}$-arylalkanediyl, $C_2$–$C_{10}$-alkenediyl or $C_8$–$C_{20}$-arylalkenediyl group which can be linear, branched or cyclic and can also contain heteroatoms such as O, S, Si, N, P or B.

For m>2, B is preferably

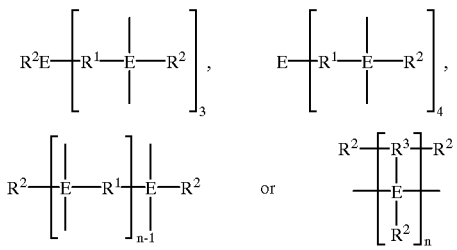

where the radicals R$^1$ are identical or different and are each a divalent $C_1$–$C_{40}$-hydrocarbon-containing bridging unit which can also contain one or more heteroatoms such as O, S, Si, Ge, N, P or B, the radials R$^2$ are identical or different and are each a hydrogen atom, a halogen atom or a $C_1$–$C_{40}$-hydrocarbon-containing radical, R$^3$ is a trivalent $C_1$–$C_{40}$-hydrocarbon-containing radical, n=m, and E are identical or different and are each, independently of one another, a carbon, silicon, germanium or tin atom.

The bonding positions on E which are left open in the formulae for B are occupied by the groups L.

Examples of $R^1$ are:

1,2-ethanediyl, 1,3-propanediyl, 1,4-butanediyl, 1,6-hexanediyl, ethylidene, 2-methyl-4-phenoxy-1,7-octanediyl, 2,5-cyclooctanediyl, 1,4-phenylene, p-xylylene, m-xylylene, o-xylylene or $(SiMe_2)_x$, where x is an integer from 0 to 100.

The radicals $R^2$ can be identical or different and are each, for example, a hydrogen atom, a halogen atom, a hydrocarbon-containing $C_1$–$C_{40}$-radical such as a $C_1$–$C_{10}$-alkyl group, a $C_1$–$C_{10}$-fluoroalkyl group, a $C_6$–$C_{20}$-, preferably $C_6$–$C_{10}$-aryl group, a $C_6$–$C_{10}$-fluoroaryl group, a $C_1$–$C_{10}$-, preferably $C_1$–$C_4$-alkoxy group, a $C_6$–$C_{10}$-aryloxy group, a $C_2$–$C_{10}$-, preferably $C_2$–$C_4$-alkenyl group, a $C_8$–$C_{12}$-, preferably $C_8$–$C_{40}$-arylalkenyl group or a $C_7$–$C_{40}$-, preferably $C_7$–$C_{12}$-alkylaryl group.

Examples of $R^2$ are:

hydrogen, chlorine, bromine, methyl, ethyl, $CF_3$, methoxy, pentafluorophenyl, Si(methyl)$_3$, tert-butyl, phenyl, p-tolyl, mesityl, iso-propyl, 1-decyl or vinyl.

$R^3$ is a trivalent hydrocarbon-containing $C_1$–$C_{40}$-radical, preferably a $C_1$–$C_{40}$-hydrocarbon radical, particularly preferably a trivalent $C_7$–$C_{40}$-alkanetriyl, $C_1$–$C_{40}$-alkylarenetriyl, $C_6$–$C_{40}$-arylalkanetriyl, $C_2$–$C_{40}$-alkenetriyl or $C_8$–$C_{40}$-arylalkenetriyl group.

Examples of $R^3$ are:

1,2,2-ethanetriyl, 1,4,4-butanetriyl, 1,6,6-hexanetriyl, 1,8,8-octanetriyl, 1,10,10-decanetriyl, 2,4-dimethyl-1,6,6-hexanetriyl, 3,5,7-tributyl-1,8,8-octanetriyl, 2,4,7-triphenyl-1,8,8-octanetriyl, 2-ethyl-1,4,4-butanetriyl.

The atoms E are identical or different, are each independent of other atoms E present in the molecule and are preferably carbon and/or silicon.

The numbering of substituent positions on preferred cyclopentadienylidene ligands L is as follows:

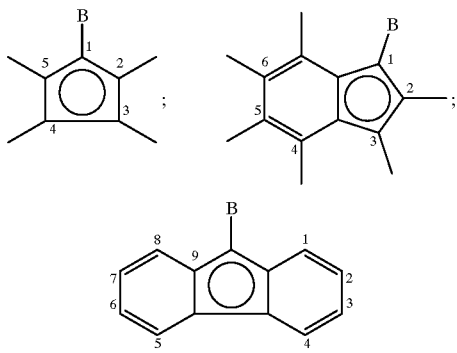

The following examples illustrate the compounds described in the formula I, but are not limiting:

tetrachloro[1-[bis($\eta^5$-1H-inden-1-ylidene)methylsilyl]-3-($\eta^5$-cyclopenta-2,4-dien-1-ylidene)-3-($\eta^5$-9H-fluoren-9-ylidene)butane]dizirconium, tetrachloro[2-[bis $\eta^5$-2-methyl-1H-inden-1-ylidene)methoxysilyl]-5-($\eta^5$-2,3,4,5-tetramethylcyclopenta-2,4-dien-1-ylidene)-5-($\eta^5$-9H-fluoren-9-ylidene)hexane]dizirconium, tetrachloro[1-[bis($\eta^5$-2-methyl-4-phenyl-1H-inden-1-ylidene)phenylgermyl]-6-($\eta^5$-cyclopenta-2,4-dien-1-ylidene)-6-($\eta^5$-9H-fluoren-9-ylidene)hexane]dizirconium tetrachloro[1-[bis($\eta^5$-4-chloro-2-methyl-1H-inden-1-ylidene)ethylsilyl]-4,5-bis($\eta^5$-2,7-di-tert-butyl-9H-fluoren-9-ylidene)pentane]dizirconium, tetrachloro[2,2-[bis($\eta^5$-1H-inden-1-ylidene)-6-($\eta^5$-2-benzylcyclopenta-2,4-dien-1-ylidene)-6-($\eta^5$-4-methoxy-1H-inden-1-ylidene)octane]dizirconium, tetrachlorol[1-[bis($\eta^5$-1H-inden-1-ylidene)methylstannyl]-7-($\eta^5$-cyclopenta-2,4-dien-1-ylidene)-7-($\eta^5$-9H-fluoren-9-ylidene)oct-4-ene]dizirconium, tetrachloro[2-[($\eta^5$-2-methyl-4-phenyl-1H-inden-1-ylidene)($\eta^5$-2-methyl-4,6-diisopropyl-1H-inden-1-ylidene)ethylstannyl]-5-($\eta^5$-cyclopenta-2,4-dien-1-ylidene)-5-($\eta^5$-1H-inden-1-ylidene)-3-phenyl-4-methoxyheptane]dizirconium, tetrachloro[1-[($\eta^5$-2,7-dimethoxy-9H-fluoren-9-ylidene)($\eta^5$-1H-inden-1-ylidene)propylsilyl]-3-($\eta^5$-cyclopenta-2,4 -dien-1-ylidene)-3-($\eta^5$-9H-fluoren-9-ylidene)butane]dizirconium, tetrachloro[1-[bis($\eta^5$-7-methyl-5-phenyl-1H-inden-1-ylidene)-tert-butylsilyl]-3-($\eta^5$-1H-inden-1-ylidene)-3-($\eta^5$-4-ethyl-9H-fluoren-9-ylidene)butane]dizirconium, tetrachloro[2-[($\eta^5$-cyclopenta-2,4-dien-1-ylidene)($\eta^5$-9H-fluoren-9-ylidene)methylsilyl]-5,5-bis($\eta^5$-2-methyl-4-naphthyl-1H-inden-1-ylidene)-5-phenylpentane]dizirconium, tetrachloro[1-[bis($\eta^5$-1H-inden-1-ylidene)methylsilyl]-6-($\eta^5$-cyclopenta-2,4-dien-1-ylidene)-6-($\eta^5$-9H-ylidene)-3-oxaheptane]dizirconium, tetrachloro[1-[bis($\eta^5$-2-methyl-1H-inden-1-ylidene)methoxysilyl]-6-($\eta^5$-2,3,4,5-tetramethylcyclopenta-2,4-dien-1-ylidene)-6-($\eta^5$-9H-fluoren-9-ylidene)-3-oxaheptane]dizirconium, tetrachloro[1-[bis($\eta^5$-2-methyl-4-phenyl-1H-inden-1-ylidene)phenylgermyl]-6-($\eta^5$-cyclopenta-2,4-dien-1-ylidene)-6-($\eta^5$-9H-fluoren-9-ylidene)-3-oxaheptane]dizirconium, tetrachloro[1-[bis($\eta^5$-4-chloro-2-methyl-1H-inden-1-ylidene)ethylsilyl]-7,8-bis($\eta^5$-2,7-di-tert-butyl-9H-fluoren-9-ylidene)-3-oxanonane]dizirconium, tetrachloro[2,2-bis($\eta^5$-1H-inden-1-ylidene)-6-($\eta^5$-2-benzylcyclopenta-2,4-dien-1-ylidene)-6-($\eta^5$-4-methoxy-1H-inden-1-ylidene)-4-oxaoctane]dizirconium, tetrachloro[1-[bis($\eta^5$-1H-inden-1-ylidene)methylstannyl]-9-($\eta^5$-cyclopenta-2,4-dien-1-ylidene)-9-($\eta^5$-9H-fluoren-9-ylidene)-5-oxadecane]dizirconium, tetrachloro-[1-[($\eta^5$-2-methyl-4-phenyl-1H-inden-1-ylidene)($\eta^5$-2-methyl-4,6-diisopropyl-1H-inden-1-ylidene)ethylstannyl]-7-($\eta^5$-cyclopenta-2,4-dien-1-ylidene)-7-($\eta^5$-1H-inden-1-ylidene)-3-oxaheptane]dizirconium, tetrachloro[1-[($\eta^5$-2,7-dimethoxy-9H-fluoren-9-ylidene)($\eta^5$-1H-inden-1-ylidene)propylsilyl]-8-($\eta^5$-cyclopenta-2,4-dien-1-ylidene)-9-($\eta^5$-9H-fluoren-9-ylidene)-4-oxanonane]dizirconium, tetrachloro[1-[bis($\eta^5$-7-methyl-5-phenyl-1H-inden-1-ylidene)-tert-butylsilyl]-5-($\eta^5$-1H-inden-1-ylidene)-5-($\eta^5$-4-ethyl-9H-fluoren-9-ylidene)-2-oxapentane]dizirconium, tetrachloro[1-[($\eta^5$-cyclopenta-2,4-dien-1-ylidene)($\eta$5-9H-fluoren-9-ylidene)methylsilyl]-6,6-bis($\eta^5$-2-methyl-4-naphthyl-1H-inden-1-ylidene)-3-oxaheptane]dizirconium, tetrachloro[1-[bis($\eta^5$-2-methyl-4,5-benzo-1H-inden-1-ylidene)methylsilyl]-8-($\eta^5$-cyclopenta-2,4-dien-1-ylidene)-8-($\eta^5$-9H-fluoren-9-ylidene)-4-isopinocamphyl-4-boranonane]dizirconium, tetrachloro[1-[bis($\eta^5$-1H-inden-1-ylidene)methylsilyl]-7-($\eta^5$-cyclopenta-2,4-dien-1-ylidene)-7-($\eta^5$-9H-fluoren-9-ylidene)-3-oxa-4-silaoctane]dizirconium, tetrachloro[1-[bis($\eta^5$-2-methyl-1H-inden-1-ylidene)methoxysilyl]-7-($\eta^5$-2,3,4,5-tetramethylcyclopenta-2,4-dien-1-ylidene)-7-($\eta^5$-9H-fluoren-9-ylidene)-3-oxa-4-silaoctane]dizirconium, tetrachloro[1-[bis($\eta^5$-2-methyl-4-phenyl-1H-inden-1-ylidene)phenylgermyl]-7-($\eta^5$-cyclopenta-2,4-dien-1- ylidene)-7-($\eta^5$-9H-fluoren-9-ylidene)-3-oxa-4-silaoctane]dizirconium,
tetrachloro[1-[bis($\eta^5$-4-chloro-2-methyl-1H-inden-1-ylidene)ethylsilyl]-8,9-bis($\eta^5$-2,7-di-tert-butyl-9H-fluoren-9-ylidene)-4-oxa-3-siladecane]dizirconium,
tetrachloro[2,2-bis($\eta^5$-1H-inden-1-ylidene)-7-($\eta^5$-2-benzylcyclopenta-2,4-dien-1-ylidene)-7-($\eta^5$-4-methoxy-1H-inden-1-ylidene)-5-oxa-4-silanonane]dizirconium,
tetrachloro[1-[bis($\eta^5$-1H-inden-1-ylidene)methylstannyl]-9-($\eta^5$-cyclopenta-2,4-dien-1-ylidene)-9-($\eta^5$-9H-fluoren-9-ylidene)-5-oxa-4-siladecane]dizirconium,
tetrachloro[1-[($\eta^5$-2-methyl-4-phenyl-1H-inden-1-ylidene)($\eta^5$-2-methyl-4,6-diisopropyl-1H-inden-1-ylidene)ethylstannyl]-7-($\eta^5$-cyclopenta-2,4-dien-1-ylidene)-7-($\eta^5$-1H-inden-1-ylidene)-3-oxa-4-silaheptane]dizirconium,
tetrachloro[1-[($\eta^5$-2,7-dimethoxy-9H-fluoren-9-ylidene)($\eta^5$-1H-inden-1-ylidene)propylsilyl]-8-(5-cyclopenta-2,4-dien-1-ylidene)-9-($\eta^5$-9H-fluoren-9-ylidene)-4-oxa-5-silanonane]dizirconium,
tetrachloro[1-[bis($\eta^5$-7-methyl-5-phenyl-1H-inden-1-ylidene)-tert-butylsilyl]-5-($\eta^5$-1H-inden-1-ylidene)-5-($\eta^5$-4-ethyl-9H-fluoren-9-ylidene)-2-oxa-3-silapentane]dizirconium,
tetrachloro[1-[($\eta^5$-cyclopenta-2,4-dien-1-ylidene) ($\eta^5$-9H-fluoren-9-ylidene)methylsilyl]-7,7-bis($\eta^5$-2-methyl-4-naphthyl-1H-inden-1-ylidene)-3-oxa-4-silaoctane]dizirconium,
tetrachloro[1-[bis($\eta^5$-1H-inden-1-ylidene)methylsilyl]-8-($\eta^5$-cyclopenta-2,4-dien-1-ylidene)-8-($\eta^5$-9H-fluoren-9-ylidene)-4,4-dimethyl-3,5-dioxa-4-silanonane]dizirconium,
tetrachloro[1-[bis($\eta^5$-2-methyl-1H-inden-1-ylidene)methoxysilyl]-7-($\eta^5$-2,3,4,5-tetramethylcyclopenta-2,4-dien-1-ylidene)-7-($\eta^5$-9H-fluaren-9-ylidene)-3,5-dioxa-4-silaoctane]dizirconium,
tetrachloro-[1-[bis($\eta^5$-2-methyl-4-phenyl-1H-inden-1-ylidene)phenylgermyl]-8-($\eta^5$-cyclopenta-2,4-dien-1-ylidene)-8-($\eta^5$-9H-fluoren-9-ylidene)-3,5-dioxa-4-silanonane]dizirconium,
tetrachloro[1-[bis($\eta^5$-4-chloro-2-methyl-1H-inden-1-ylidene)ethylsilyl]-8,9-bis($\eta^5$-2,7-di-tert-butyl-9H-fluoren-9-ylidene)-4,6-dioxa-5-siladecane]dizirconium,
tetrachloro[2,2-bis($\eta^5$-1H-inden-1-ylidene)-10-($\eta^5$-2-benzylcyclopenta-2,4-dien-1-ylidene)-10-($\eta^5$-4-methoxy-1H-inden-1-ylidene)-5,7-dioxa-6-siladecane]dizirconium,
tetrachloro[1-[bis($\eta^5$-1H-inden-1-ylidene)methylstannyl]-9-($\eta^5$-cyclopenta-2,4-dien-1-ylidene)-9-($\eta^5$-9H-fluoren-9-ylidene)-3,5-dioxa-4-siladecane]dizirconium,
tetrachloro[1-[($\eta^5$-2-methyl-4-phenyl-1H-inden-1-ylidene)($\eta^5$-2-methyl-4,6-diisopropyl-1H-inden-1-ylidene)ethylstannyl]-7-($\eta^5$-cyclopenta-2,4-dien-1-ylidene)-7-($\eta^5$-1H-inden-1-ylidene)-4,6-dioxa-5-siladecane]dizirconium,
tetrachloro[1-[($\eta^5$-2,7-dimethoxy-9H-fluoren-9-ylidene)($\eta^5$-1H-inden-1-ylidene)propylsilyl]-8-($\eta^5$-cyclopenta-2,4-dien-1-ylidene)-9-($\eta^5$-9H-fluoren-9-ylidene)-3,5-dioxa-4-silanonane]dizirconium,
tetrachloro[1-[bis($\eta^5$-7-methyl-5-phenyl-1H-inden-1-ylidene)-tert-butylsilyl]-5-($\eta^5$-1H-inden-1-ylidene)-5-($\eta^5$-4-ethyl-9H-fluoren-9-ylidene)-2,4-dioxa-3-silapentane]dizirconium,
tetrachloro[1-[($\eta^5$-cyclopenta-2,4-dien-1-ylidene) ($\eta^5$-9H-fluoren-9-ylidene)methylsilyl]-9,9-bis($\eta^5$-2-methyl-4-naphthyl-1H-inden-1-ylidene)-3,5-dioxa-4-siladecane]dizirconium,
tetrachloro[4-($\eta^5$-cyclopenta-2,4-dien-1-ylidene)-4-($\eta^5$-9H-fluoren-9-ylidene)-1,1-bis($\eta^5$-1H-inden-1-ylidene)silacyclohexane]dizirconium,
tetrachloro[1,1-bis($\eta^5$-2-methyl-1H-inden-1-ylidene)-4-($\eta^5$-2,3,4,5-tetramethylcyclopenta-2,4-dien-1-ylidene)-4-($\eta^5$-9H-fluoren-9-ylidene)silacycloheptane]dizirconium,
tetrachloro[1,1-bis($\eta^5$-2-methyl-4-phenyl-1H-inden-1-ylidene)-4-($\eta^5$-cyclopenta-2,4-dien-1-ylidene)-4-($\eta^5$-9H-fluoren-9-ylidene)silacyclohexane]dizirconium,
tetrachloro[7,7-bis($\eta^5$-4-chloro-2-methyl-1H-inden-1-ylidene)-1,2-bis($\eta^5$-2,7-di-tert-butyl-9H-fluoren-9-ylidene)silacyclonon-4-ene]dizirconium,
tetrachloro[1,1-bis($\eta^5$-1H-inden-1-ylidene)-5-($\eta^5$-2-benzylcyclopenta-2,4-dien-1-ylidene)-5-($\eta^5$-4-methoxy-1H-inden-1-ylidene)silacyclohexane]dizirconium,
tetrachloro1,1-bis($\eta^5$-1H-inden-1-ylidene)-7-($\eta^5$-cyclopenta-2,4-dien-1-ylidene)-7-($\eta^5$-9H-fluorea-9-ylidene)silacyclohexane]dizirconum,
tetrachloro[1-($\eta^5$-2-methyl-4-phenyl-1H-inden-1-ylidene)-2-($\eta^5$-2-methyl-4,6-diisopropyl-1H-inden-1-ylidene)-6-($\eta^5$-cyclopenta-2,4-dien-1-ylidene)-6-($\eta^5$-1H-inden-1-ylidene)-4-phenyl-7-methoxy-1-silacyclodeca-4,8-dien]dizirconium,
tetrachloro[1-($\eta^5$-2,7-dimethoxy-9H-fluoren-9-ylidene)-2-($\eta^5$-1H-inden-1-ylidene)-4-($\eta^5$-cyclopenta-2,4-dien-1-ylidene)-5-($\eta^5$-9H-fluoren-9-ylidene)cyclohexane]dizirconium,
tetrachloro[1,1-bis($\eta^5$-7-methyl-5-phenyl-1H-inden-1-ylidene)-3-($\eta^5$-1H-inden-1-ylidene)-3-($\eta^5$-4-ethyl-H-fluoren-9-ylidene)-5-oxacycloheptane]dizirconium,
tetrachloro[2-($\eta^5$-cyclopenta-2,4-dien-1-ylidene)-2-($\eta^5$-9H-fluoren-9-ylidene)-5,5-bis($\eta^5$-2-methyl-4-naphthyl-1H-inden-1-ylidene)-3,4-diethylcyclooctane]dizirconium,
tetrachloro[1-[1,2-bis($\eta^5$-1H-inden-1-ylidene)-1,2,2-trimethyldisilane-1-yl]-3-($\eta^5$-cyclopentane-2,4-dien-1-ylidene)-4-($\eta^5$-9H-fluoren-9-ylidene)-3,4dimethylpentane]dizirconium,
tetrachloro[1-[1,2-bis($\eta^5$-2-methyl-1H-inden-1-ylidene)-1,2,2-trimethyldisilane-1-yl]-6-($\eta^5$-2,3,4,5-tetramethylcyclopenta-2,4-dien-1-ylidene)-7-($\eta^5$-9H-fluoren-9-ylidene)-6,7-dimethoxyethane]dizirconium,
tetrachloro[1-[1,2-bis($\eta^5$-2-methyl-4-phenyl-1H-inden-1-ylidene)-1,2,2-triphenyldigerman-1-yl]-3-($\eta^5$-cyclopenta-2,4-dien-1-ylidene)-4-($\eta^5$-9H-fluoren-9-ylidene)-3-methyl-4-phenylpentane]dizirconium,
tetrachloro[1-[1,2-bis($\eta^5$-2,7-di-tert-butyl-9H-fluoren-9-ylidene)-1,2,2-trimethyldisilane-1-yl]-3,4-bis($\eta^5$-4-chloro-2-methyl-1H-inden-1-ylidene)-3,4-dimethylpentane]dizirconium,
tetrachloro[1-(1-($\eta^5$-1H-inden-1-ylidene)-2-($\eta^5$-2-benzylcyclopenta-2,4-dien-1-ylidene)-1,2,2-trimethyldisilane-1-yl]-3-($\eta^5$-2-benzylcyclopenta-2,4-dien-1-ylidene)-4-($\eta^5$-4-methoxy-1H-inden-1-ylidene)-4,5-dimethylhexane]dizirconium,
tetrachloro[2,3-[bis($\eta^5$-1H-inden-1-ylidene)]-8-($\eta^5$-cyclopenta-2,4-dien-1-ylidene)-9-($\eta^5$-9H-fluoren-9-ylidene)-3,5,8-trimethyl-3-siladecane]dizirconium,
tetrachloro[2-[$\eta^5$-2-methyl-4-phenyl-1H-inden-1-ylidene)]-3-($\eta^5$-2-methyl-4,6-diisopropyl-1H-inden-1-ylidene)-8-($\eta^5$-cyclopenta-2,4-dien-1-ylidene)-9-($\eta^5$-1H-inden-1-ylidene)-3,5,8-triphenyl-3-stannadecane]dizirconium,
octachloro[2,10-bis[bis($\eta^5$-1H-inden-1-ylidene)methylsilyl]-6,14-bis[1-($\eta^5$-7-methyl-5-phenyl-1H-inden-1-ylidene)-1-($\eta^5$-9H-fluoren-9-ylidene)ethyl]pentadecane]tetrazirconium,
octachloro[2-[bis($\eta^5$-2-methyl-4-naphthyl-1H-inden-1-ylidene)methylsilyl]-10-[bis($\eta^5$-cyclopenta-2,4-dien-1-ylidene)methylsilyl]-6,14-bis[1-($\eta^5$-cyclopenta-2,4-dien-1-ylidene)-1-($\eta^5$-9H-fluoren-9-ylidene)ethyl]pentadecane]tetrazirconium,
octachloro[3-[bis($\eta^5$-2-methyl-4-naphthyl-1H-inden-1-ylidene)methylsilyl]-7-[bis($\eta^5$-cyclopenta-2,4-dien-1-ylidene)methylsilyl]-15-[1-($\eta^5$-cyclopenta-2,4-dien-1-ylidene)-1-($\eta^5$-9H-fluoren-9-ylidene)ethylioctadecane]tetrazirconium, octachloro[3-[bis($\eta^5$-2-methyl-4-naphthyl-1H-inden-1-ylidene)methylsilyl]-7-[bis($\eta^5$-cyclopenta-2,4-dien-1-ylidene)methylsilyl]-15-[1-($\eta^5$-cyclopenta-2,4-dien-1-ylidene)-1-($\eta^5$-9H-fluoren-9-ylidene)ethyl]-5,12-dimethyl-8-phenoxy-16-(1-naphthyl)octadecane]tetrazirconium, octachloro[2-[bis($\eta^5$-2-methyl-4-naphthyl-1H-inden-1-ylidene)methylsilyl]-7-[bis($\eta^5$-cyclopenta-2,4-dien-1-ylidene)methylsilyl]-8-[bis($\eta^5$-2-methyl-4-phenyl-1H-inden-1-ylidene)phenylgermyl]-15-[1-($\eta^5$-cyclopenta-2,4-dien-1-ylidene)-1-($\eta^5$-9H-fluoren-9-ylidene)ethyl]-16-[bis($\eta^5$-2-methyl-4,6-diisopropyl-1H-inden-1-ylidene)methoxysilyl]octadecane]tetrazirconium, octachloro[2,2,8,8-tetrakis($\eta^5$-1H-inden-1-ylidene)-5,11-bis($\eta^5$-cyclopenta-2,4-dien-1-ylidene)-5,11-bis($\eta^5$-9H-fluoren-9-ylidene)-2,8-disiladodecane]tetrazirconium, octachloro[2,3,8,8-tetrakis($\eta^5$-1H-inden-1-ylidene)-5,11-bis($\eta^5$-cyclopenta-2,4-dien-1-ylidene)-5,12-bis($\eta^5$-9H-fluoren-9-ylidene)-2,8-disilatetradecane]tetrazirconium and octachloro[2,9-bis($\eta^5$-2-methyl-1H-inden-1-ylidene)-2,9-bis($\eta^5$-9H-fluoren-9-ylidene)-5,11-bis($\eta^5$-cyclopenta-2,4-dien-1-ylidene)-5,11-bis($\eta^5$-2,3,4,5-tetramethylcyclopenta-2,4-dien-1-ylidene)-2,9-disiladodecane]tetrazirconium.

The metallocenes of the invention can be synthesized by various routes. Examples are: the ligand system is synthesized via a plurality of steps from readily obtainable precursors. The ligand system is reacted with a base, e.g. butyllithium, to give the polylithium salt and subsequently with a metal halide, e.g. zirconium tetrachloride, to give the multinucleic metallocene.

The synthesis of ligand systems having more than two metallocene fragments L—MX$_2$—L is shown schematically by means of a number of general examples. These symbols are defined as in the description of the invention. These examples serve to illustrate and in no way restrict the scope of the invention.

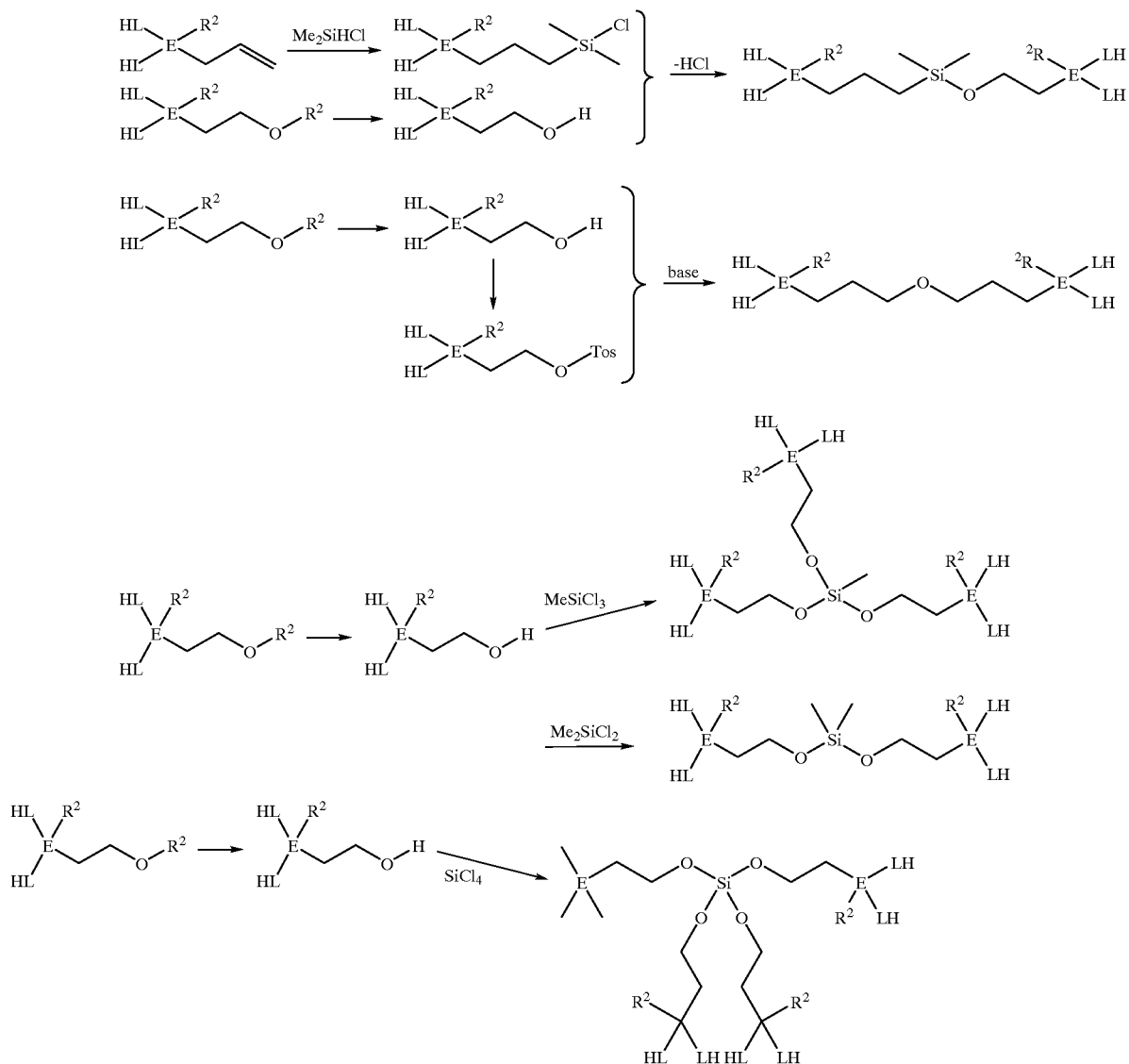

The reaction of these ligand systems to give the metallocenes of the invention is shown in the following reaction scheme:

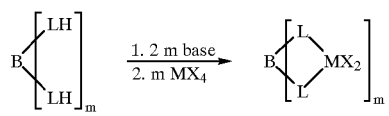

In addition, it is possible to synthesize functionalized multinucleic metallocene complexes having polymerizable side groups or having side groups which make possible selective or unselective chemical linking to form higher molecular weight metallocenes. The product can here consist of a mixture of different multinucleic metallocenes, with the ratio of the different metallocene fragments being determined by the stoichiometry of the starting materials prior to the coupling reaction. The general reaction schemes serve only to illustrate by way of example and in no way restrict the scope of the invention. x and y are integers from 1 to 100,000.

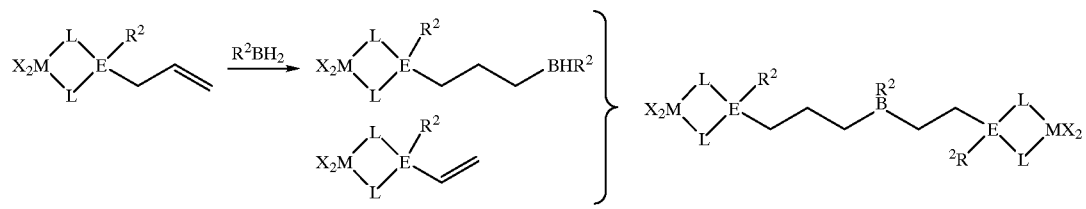

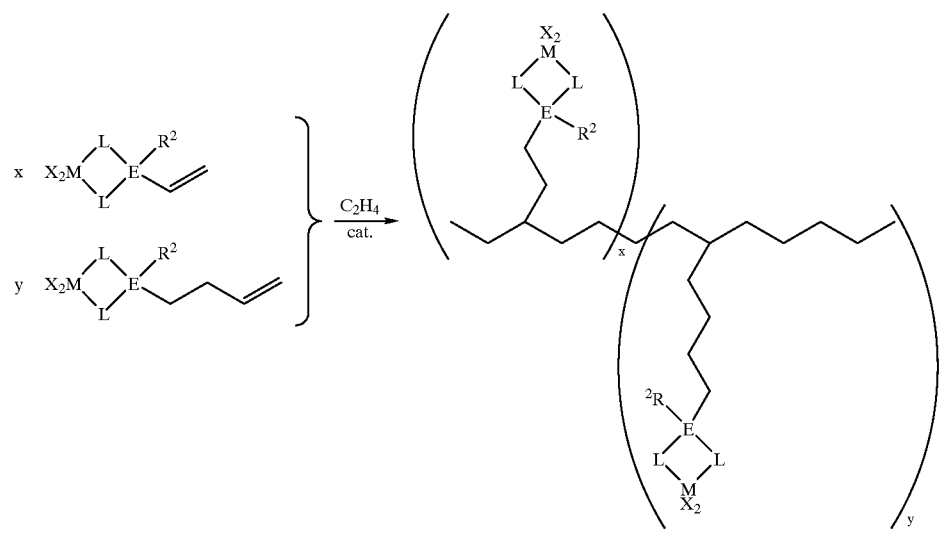

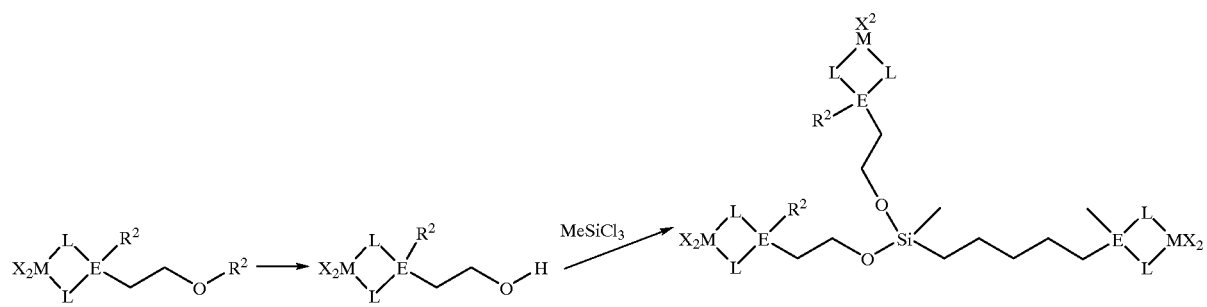

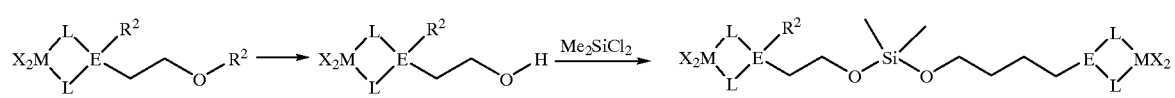

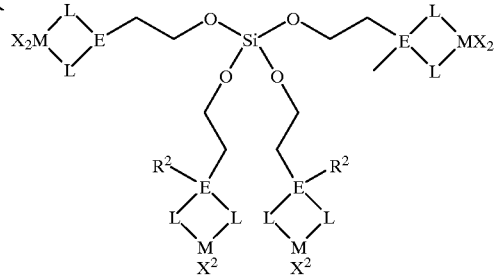

The present invention also provides a process for preparing an olefin polymer by polymerization of an least one olefin in the presence of a catalyst comprising at least one metallocene compound and a cocatalyst, wherein the metallocene is a compound of the formula I. The polymerization can be a homopolymerization or a copolymerization.

Preference is given to homopolymerizing or copolymerizing olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinylnorbornene. In the process of the invention, preference is given to homopolymerizing ethylene or copolymerizing ethylene with one or more 1-olefins having from 3 to 20 carbon atoms, for example propylene, and/or one or more dienes having from 4 to 20 carbon atoms, for example 1,4-butadiene. Examples of such copolymers are ethylenepropylene copolymers and ethylene-propylene-1,4-hexadiene copolymers.

The polymerization is preferably carried out at a temperature of from −60 to 250° C., particularly preferably from 50 to 200° C. The pressure is preferably from 0.5 to 64 bar.

The polymerization can be carried out in solution, in bulk, in suspension or in the gas phase, continuously or batchwise, in one or more stages. A preferred embodiment is gas-phase polymerization.

The catalyst used in the process of the invention preferably comprises one metallocene compound of the formula I.

In principle, a suitable cocatalyst in the process of the invention is any compound which, owing to its Lewis acidity, can convert the neutral metallocene into a cation and stabilize the latter ("labile coordination"). Furthermore, the cocatalyst or the anion formed therefrom should undergo no further reactions with the metallocene cation formed (EP 427 697). The cocatalyst is preferably an aluminum compound or a mixture of a plurality of aluminum compounds and/or a boron compound or a mixture of a plurality of boron compounds.

The boron compound preferably has the formula $R^4{}_x NH_{4-x} BR^5{}_4$, $R^4{}_x PH_{4-x} BR^5{}_4$, $R^4{}_3 CBR^5{}_5$ or $BR^5{}_3$, where x is a number from 1 to 4, preferably 3, the radicals $R^4$ are identical or different, preferably identical, and are $C_1$–$C_{10}$-alkyl or $C_6$–$C_{18}$-aryl radicals, or two radicals $R^4$ together with the atoms connecting them form a ring, and the radicals $R^5$ are identical or different, preferably identical, and are $C_6$–$C_{18}$-aryl which can be substituted by alkyl, haloalkyl or fluorine. In particular, $R^4$ is ethyl, propyl, butyl or phenyl and $R^5$ is phenyl, pentafluorophenyl, 3,5-bistrifluoromethylphenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula IIa for the linear type and/or the formula IIb for the cyclic type,

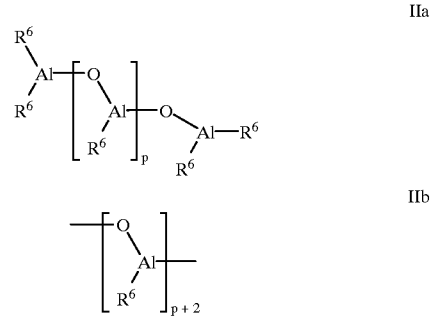

where, in the formulae IIa and IIb, the radicals $R^6$ are identical or different and are each hydrogen or a $C_1$–$C_{18}$-alkyl group or a $C_6$–$C_{18}$-aryl group or benzyl, and p is an integer from 2 to 50, preferably from 10 to 35.

The radicals $R^6$ are preferably identical and are hydrogen, methyl, isobutyl, phenyl or benzyl, particularly preferably methyl.

The methods of preparing the aluminoxanes are known (DE 4 004 477).

The exact spatial structure of the aluminoxane is not known (J. Am. Chem. Soc, 115 (1993) 4971). For example, it is conceivable that chains and rings are connected to form larger two-dimensional or three-dimensional structures.

Regardless of the manner of preparation, all aluminoxane solutions have in common a varying content of unreacted aluminum starting compound which is present in free form or as adduct.

Before use in the polymerization, it is possible to preactivate the metallocene compound of the invention using a cocatalyst, in particular an aluminoxane. This significantly increases the polymerization activity. The preactivation of the metallocene compound is preferably carried out in solution. In this procedure, the metallocene compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of from $10^4$ to 1 mol per mol of aluminum. The preactivation time is from 5 minutes to 60 hours, preferably from 5 to 60 minutes. The preactivation is carried out at a temperature of from −78 to 100° C., preferably from 0 to 70° C.

The metallocene compound is here preferably used in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is preferably used in a concentration of from $10^{-6}$ to $10^{-1}$ mol, particularly preferably from 10 to 10 mol, per $dm^3$ of solvent or per $dm^3$ of reactor volume. The other specified cocatalysts and/or scavengers are used in approximately equimolar amounts to the metallocene compound. However, higher concentrations are also possible in principle.

To remove catalyst poisons present in the olefin, purification using an aluminum compound, preferably an aluminum alkyl such as trimethylaluminum, triisobutylaluminum or triethylaluminum, is advantageous (scavenger function). This purification can be carried out either in the polymerization system itself or the olefin is, prior to addition to the polymerization system, brought into contact with the aluminum compound and subsequently separated off again.

In the process of the invention, hydrogen can be added as a molecular weight regulator and/or to increase the activity. This enables low molecular weight polyolefins such as waxes to be obtained.

The metallocene compound is, in the process of the present invention, preferably reacted with one or more cocatalysts outside the polymerization reactor in a separate step using a suitable solvent. Application to a support can be carried out during this step. The supported catalyst can be used in the reaction medium in the presence of a scavenger, e.g. an aluminum alkyl such as triethylaluminum, triisobutylaluminum, etc.

In the process of the invention, a prepolymerization can be carried out by means of the metallocene compound. For the prepolymerization, the olefin (or one of the olefins) used in the polymerization is preferably employed.

The catalyst used in the process of the invention can be supported. The application to a support allows, for example, the particle morphology of the polyolefin prepared to be controlled. The metallocene compound can here first be reacted with the support and subsequently with the cocatalyst. The cocatalyst can also be supported first and subsequently reacted with the metallocene compound. It is also possible to support the reaction product of metallocene compound and cocatalyst. Suitable support materials are, for example, silica gels, aluminum oxides, solid aluminoxane or other inorganic support materials such as magnesium chloride. Another suitable support material is a polyolefin powder in finely divided form. The preparation of the supported catalyst can be carried out, for example, as described in EP 567 952.

If the polymerization is carried out as a suspension or solution polymerization, an inert solvent customary for the Ziegler low-pressure process is used. For example, the polymerization is carried out in an aliphatic or cycloaliphatic hydrocarbon; examples of such hydrocarbons which may be mentioned are propane, butane, hexane, heptane, isooctane, cyclohexane, methylcyclohexane. It is also possible to employ a petroleum or hydrogenated diesel oil fraction. Toluene can also be used. The polymerization is preferably carried out in the liquid monomer.

If inert solvents are used, the monomers are metered in in gaseous or liquid form.

The polymerization time can be any desired, since the catalyst system to be used in the process of the invention shows only a slight time-dependent drop in the polymerization activity.

The polymer products prepared according to the process of the invention are particularly suitable for producing shaped bodies such as films, sheets, fibers or large hollow bodies (e.g. pipes).

The metallocene compound of the invention allows the preparation of polymer mixtures which are formed uniformly in all polymer particles in the desired composition independent of the supporting process.

In particular, it is possible to obtain polymer mixtures which have compositions defined independently of the supporting process and are in uniformly mixed form (optimum mixing) in the polymer particle.

The polyolefin mixtures prepared using the metallocenes of the invention comprise polymer components which can differ in terms of various features, e.g. molecular weight, molecular weight distribution, tacticity (e.g. isotactic, syndiotactic, hemiisotactic, atactic), degree of tacticity (e.g. syndiotacticity index, isotacticity index), comonomer content (e.g. high ethylene incorporation, low ethylene incorporation), manner in which the comonomer is incorporated (e.g. randomly, in the form of blocks).

EXAMPLES

Preparation and handling of organometallic compounds were carried out with exclusion of air and moisture under argon protective gas (Schlenk technique). All solvents required were dried before use by boiling for a number of hours over suitable desiccants and subsequent distillation under argon.

Toluene-soluble methylaluminoxane is procured as a 10% strength toluene solution from WITCO and, according to an aluminum determination, contains 36 mg of Al/ml.

1. Tetrachloro[1-[bis($\eta^5$-2-methyl-4,5-benzo-1H-inden-1-ylidene)methylsilyl]-8-($\eta^5$-cyclopenta-2,4-dien-1-ylidene)-8-($\eta^5$-9H-fluoren-9-ylidene)-4-isopinocamphyl-4-boranonane]dizirconium A solution of 2.0 g (4.4 mmol) of dichloro[4-($\eta^5$-cyclopenta-2,4-dien-1-ylidene)-4-($\eta^5$-9H-fluoren-9-ylidene)-1-pentene]zirconium in 100 ml of toluene is added dropwise at −30° C. to a THF solution of isopinocamphylborane (4.4 mmol; prepared from α-pinene and borane). The solution is subsequently warmed to 0° C. and left stirring for a further 12 hours at this temperature. Subsequently, a solution of dichloro[bis($\eta^5$-2-methyl-4,5-benzo-1H-inden-1-ylidene)methyl(3-propenyl)silane]zirconium (2.6 g; 4.4 mmol) in toluene is added to the above solution. The mixture is left stirring for a further 12 hours at room temperature. The solvent is removed under reduced pressure from the clear solution until it starts to become turbid and the suspension is subsequently crystallized by storage at −30° C. Filtration and washing with pentane gives 3.3 g (63%) of tetrachloro[1-[bis($\eta^5$-2-methyl-4,5-benzo-1H-inden-1-ylidene)methylsilyl]-8-($\eta^5$-cyclopenta-2,4-dien-1-ylidene)-8-($\eta^5$-9H-fluoren-9-ylidene)-4-isopinocamphyl-4-boranonane]dizirconium as a yellow solid.

2. Tetrachloro[1-[bis($\eta^5$-H-inden-1-ylidene)methylsilyl-9-($\eta^5$-cyclopenta-2,4-dien-1-ylidene)-9-($\eta^5$-9H-fluoren-9-ylidene)-4-oxa-5-silaoctane]dizirconium In the presence of a cation exchanger loaded with sodium ions, a solution of 3.0 g (5.4 rmol) of dichloro[4-($\eta^5$- cyclopenta-2,4-dien-1-ylidene)-4-(5-9H-fluoren-9-ylidene)-1-(chlorodimethylsilyl)pentane]zirconium in 40 ml of THP is reacted at 45° C. with a suspension of 2.7 g (5.4 mmol) of dichloro[bis($\eta^5$-1H-inden-1ylidene)methyl(3-hydroxypropyl)silane]zirconium in 40 ml of THF. After one hour, the ion exchanger is filtered off, the solvent is taken off under reduced pressure and the residue is extracted with methylene chloride. The product precipitates at −30° C. as an orange-yellow solid. This gives 1.9 g (35%) of tetrachloro[1-[bis($\eta^5$-1H-inden-1-ylidene)methylsilyl]-9-($\eta^5$-cyclopenta-2,4-dien-1-ylidene)-9-($\eta^5$-9H-fluoren-9-ylidene)-4-oxa-5-silaoctane]dizirconium.

What is claimed is:

1. A metallocene compound containing at least two metallocene fragments L—MX$_2$—L which contain the same metal atom M and which are different from one another and having the formula I

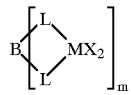

(I)

where B is a bridging unit, m is an integer from 2 to 100,000, M is a metal atom of group IVb, Vb or VIb of the Periodic Table of the Elements, X are identical or different in one metallocene fragment L—MX$_2$—L and are each, independently of one another, hydrogen, a $C_1$–$C_{40}$-hydrocarbon-containing group, an OH group, a halogen atom or a pseudo-halogen, L are identical or different in one metallocene fragment L—MX$_2$—L and are each, independently of one another, a π ligand or another electron donor.

2. A catalyst component comprising at least one metallocene compound as claimed in claim 1 and at least one cocatalyst.

3. A catalyst component as claimed in claim 2 additionally containing a support.

4. A process for preparing an olefin polymer by polymerization of at least one olefin in the presence of a catalyst comprising at least one metallocene compound and at least one cocatalyst, wherein the metallocene is a compound of the formula I as claimed in claim 1.

5. The metallocene as claimed in claim 1, wherein M is titanium, zirconium, hafnium, vanadium, niobium, tantalum, chromium, molybdenum or tungsten.

6. The metallocene as claimed in claim 5, wherein M is a zirconium, hafnium or titanium and the radicals X are each are each hydrogen, $C_1$–$C_{10}$-alkyl group, a $C_1$–$C_{10}$-alkoxy group, a $C_6$–$C_{10}$-aryl group and $C_6$–$C_{10}$-aryloxy group, a $C_2$–$C_{10}$-alkenyl group, a $C_7$–$C_{40}$-arylalkyl group, a $C_7$–$C_{40}$-arylalkyl, a $C_8$–$C_{40}$-arylalkenyl group, an OH group, a fluorine, chlorine, bromine, iodine, or nitrile.

7. The compound as claimed in claim 6, wherein the radicals X are each a hydrogen atom, a $C_1$–$C_4$-alkyl group, a $C_1$–$C_3$-alkoxy group, a $C_6$–$C_8$-aryloxy group, a $C_2$–$C_4$-alkenyl group, a $C_7$–$C_{12}$-arylalkyl group, a $C_7$–$C_{12}$-alkylaryl group, a $C_8$–$C_{12}$-arylalkenyl group, chlorine or nitrile.

8. The compound as claimed in claim 7, wherein L is selected from the group consisting of tert-butylamido, cyclohexylamido, phenylamido, 2-6-diisopropylphenylamido, 2,6-di-tert-butylphenylamido, cyclododecylamido, cyclopentadienylidene, and a substituted cyclopentadienylidene group.

9. The compound as claimed in claim 7, wherein L is selected from the group consisting of tetramethylcyclopentadienylidene, methylcyclopentadienylidene, methyl-tert-butylcylopentadienylidene, tert-butylcyclopentadienylidene, isopropylcyclopentadienylidene, dimethylcyclopentadienylidene, trimethylcyclopentadienylidene, phenylcyclopentadienylidene, diphenylcyclopentadienylidene, indenylidene, 2-methylindenylidene, 2-ethylindenylidene, 3-methylindenylidene, 3-tert-butylindenylidene, 3-trimethylsilylindenylidene, 2-methyl-4-phenylindenylidene, 2-ethyl-4-phenylindenylidene, 2-methyl-4-naphthylindenylidene, 2-methyl-4-isopropylindenylidene, 4,5-benzoindenylidene, 2-methyl-4,5-benzoindenylidene, 2-methyl-α-acenaphthylindenylidene, 2-methyl-4,6-diisopropylindenylidene, fluorenylidene, 4-methylfluorenylidene and 2,7-di-tert-butylfluorenylidene.

10. The compound as claimed in claim 6, wherein B is

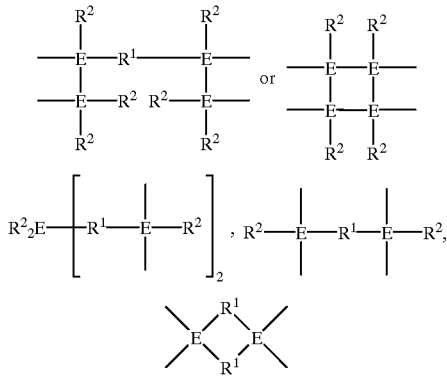

where the radicals $R^1$ are identical or different and are each a divalent $C_1$–$C_{40}$-hydrocarbon-containing bridging unit which can also contain one or more heteroatoms, the radicals $R^2$ are identical or different and are each a hydrogen atom, a halogen atom or a $C_1$–$C_{40}$-hydrocarbon-containing radical, and E are identical or different and are each, independently of one another, a carbon, silicon, germanium or tin atom.

11. A compound selected from the group consisting of tetrachloro[1-[bis($\eta^5$-1H-inden-1-ylidene)methylsilyl]-3-($\eta^5$-cyclopenta-2,4-dien-1-ylidene)-3-($\eta^5$-9H-fluoren-9-ylidene)butane]dizirconium, tetrachloro[2-[bis($\eta^5$-2-methyl-1H-inden-1-ylidene)methoxysilyl]-5-($\eta^5$-2,3,4,5-tetramethylcyclopenta-2,4-dien-1-ylidene)-5-($\eta^5$-9H-fluoren-9-ylidene)hexane]dizirconium, tetrachloro[1-[bis($\eta^5$-2-methyl-4-phenyl-1H-inden-1-ylidene)phenylgermyl]-6-($\eta^5$-cyclopenta-2,4-dien-1-ylidene)-6-($\eta^5$-9H-fluoren-9-ylidene)hexane]dizirconium tetrachloro[1-[bis($\eta^5$-4-chloro-2-methyl-1H-inden-1-ylidene)ethylsilyl]-4,5-bis($\eta^5$-2,7-di-tert-butyl-9 H-fluoren-9-ylidene)pentane]dizirconium, tetrachloro[2,2-[bis($\eta^5$-1H-inden-1-ylidene)-6-($\eta^5$-2-benzylcyclopenta-2,4-dien-1-ylidene)-6-($\eta^5$-4-methoxy-1H-inden-1-ylidene)octane]dizirconium, tetrachloro[1-[bis($\eta^5$-1H-inden-1-ylidene)methylstannyl]-7-($\eta^5$-cyclopenta-2,4-dien-1-ylidene)-7-($\eta^5$-9H-fluoren-9-ylidene)oct-4-ene]dizirconium, tetrachloro[2-[$\eta^5$-2-methyl-4-phenyl-1H-inden-1-ylidene)($\eta^5$-2-methyl-4,6-diisopropyl-1H-inden-1-ylidene)ethylstannyl]-5-($\eta^5$-cyclopenta-2,4-dien-1-ylidene)-5-($\eta^5$-1H-inden-1-ylidene)-3-phenyl-4-methoxyheptane]dizirconium, tetrachloro[1-[($\eta^5$-2,7-dimethoxy-9H-fluoren-9-ylidene)($\eta^5$-1H-inden-1-ylidene)propylsilyl]-3-($\eta^5$-cyclopenta-2,4-dien-1-ylidene)-3-($\eta^5$-9H-fluoren-9-ylidene)butane]dizirconium, tetrachloro[1-[bis($\eta^5$-7-methyl-5-phenyl-1H-inden-1-ylidene)-tert-butylsilyl]-3-($\eta^5$-1H-inden-1-ylidene)-3-($\eta^5$-4-ethyl-9H-fluoren-9-ylidene)butane]dizirconium, tetrachloro[2-[($\eta^5$-cyclopenta-2,4-dien-1-ylidene)($\eta^5$-9H-fluoren-9-ylidene)methylsilyl]-5,5-bis($\eta^5$-2-methyl-4-naphthyl-1H-inden-1-ylidene)-5-phenylpentane]dizirconium, tetrachloro[1-[bis($\eta^5$-1H-inden-1-ylidene)methylsilyl]-6-($\eta^5$-cyclopenta-2,4-dien-1-ylidene)-6-($\eta^5$-9H-ylidene)-3-oxaheptane]dizirconium, tetrachloro[1-[bis($\eta^5$-2-methyl-1H-inden-1-ylidene)methoxysilyl]-6-($\eta^5$-2,3,4,5-tetramethylcyclopenta-2,4-dien-1-ylidene)-6-($\eta^5$-9H-fluoren-9-ylidene)-3-oxaheptane]dizirconium, tetrachloro[1-[bis($\eta^5$-2-methyl-4-phenyl-1H-inden-1-ylidene)phenylgermyl]-6-($\eta^5$-cyclopenta-2,4-dien-1-ylidene)-6-($\eta^5$-9H-fluoren-9-ylidene)-3-oxaheptane]dizirconium, tetrachloro[1-[bis($\eta^5$-4-chloro-2-methyl-1H-inden-1-ylidene)ethylsilyl]-7,8-bis($\eta^5$-2,7-di-tert-butyl-9H-fluoren-9-ylidene)-3-oxanonane]dizirconium, tetrachloro[2,2-bis($\eta^5$-1H-inden-1-ylidene)-6-($\eta^5$-2-benzylcyclopenta-2,4-dien-1-ylidene)-6-($\eta^5$-4-methoxy-1H-inden-1-ylidene)-4-oxaoctane]dizirconium, tetrachloro[1-[bis($\eta^5$-1H-inden-1-ylidene)methylstannyl]-9-($\eta^5$-cyclopenta-2,4-dien-1-ylidene)-9-($\eta^5$-9H-fluoren-9-ylidene)-5-oxadecane]dizirconium, tetrachloro-[1-[($\eta^5$-2-methyl-4-phenyl-1H-inden-1-ylidene)($\eta^5$-2-methyl-4,6-diisopropyl-1H-inden-1-ylidene)ethylstannyl]-7-($\eta^5$-cyclopenta-2,4-dien-1-ylidene)-7-($\eta^5$-1H-inden-1-ylidene)-3-oxaheptane]dizirconium, tetrachloro[1-[($\eta^5$-2,7-dimethoxy-9H-fluoren-9-ylidene)($\eta^5$-1H-inden-1-ylidene)propylsilyl]-8-($\eta^5$-cyclopenta-2,4-dien-1-ylidene)-9-($\eta^5$-9H-fluoren-9-ylidene)-4-oxanonane]dizirconium, tetrachloro[1-[bis($\eta^5$-7-methyl-5-phenyl-1H-inden-1-ylidene)-tert-butylsilyl]-5-[($\eta^5$-1H-inden-1-ylidene)-5-($\eta^5$-4-ethyl-9H-fluoren-9-ylidene)-2-oxapentane]dizirconium, tetrachloro[1-[($\eta^5$-cyclopenta-2,4-dien-1-ylidene)($\eta^5$-9H-fluoren-9-ylidene)methylsilyl]-6,6-bis($\eta^5$-2-methyl-4-naphthyl-1H-inden-1-ylidene)-3-oxaheptane]dizirconium, tetrachloro[1-[bis($\eta^5$-2-methyl-4,5-benzo-1H-inden-1-ylidene)methylsilyl]-8-($\eta^5$-cyclopenta-2,4-dien-1-ylidene)-8-($\eta^5$-9H-fluoren-9-ylidene)-4-isopinocamphyl-4-borananone]dizirconium, tetrachloro[1-[bis($\eta^5$-1H-inden-1-ylidene)methylsilyl]-7-($\eta^5$-cyclopenta-2,4-dien-1-ylidene)-7-($\eta^5$-9H-fluoren-9-ylidene)-3-oxa-4-silaoctane]dizirconium, tetrachloro[1-[bis($\eta^5$-2-methyl-1H-inden-1-ylidene)methoxysilyl]-7-($\eta^5$-2,3,4,5-tetramethylcyclopenta-2,4-dien-1-ylidene)-7-($\eta^5$-9H-fluoren-9-ylidene)-3-oxa-4-silaoctane]dizirconium, tetrachloro[1-[bis($\eta^5$-2-methyl-4-phenyl-1H-inden-1-ylidene)phenylgermyl]-7-($\eta^5$-cyclopenta-2,4-dien-1-ylidene)-7-($\eta^5$-9H-fluoren-9-ylidene)-3-oxa-4-silaoctane]dizirconium, tetrachloro[1-[bis($\eta^5$-4-chloro-2-methyl-1H-inden-1-ylidene)ethylsilyl]-8,9-bis($\eta^5$-2,7-di-tert-butyl-9H-fluoren-9-ylidene)-4-oxa-3-siladecane]dizirconium, tetrachloro[2,2-bis($\eta^5$-1H-inden-1-ylidene)-7-($\eta^5$-2-benzylcyclopenta-2,4-dien-1-ylidene)-7-($\eta^5$-4-methoxy-1H-inden-1-ylidene)-5-oxa-4-silanonane]dizirconium, tetrachloro[1-[bis($\eta^5$-1H-inden-1-ylidene)methylstannyl]-9-($\eta^5$-cyclopenta-2,4-dien-1-ylidene)-9-($\eta^5$-9H-fluoren-9-ylidene)-5-oxa-4-siladecane]dizirconium, tetrachloro[1-[($\eta^5$-2-methyl-4-phenyl-1H-inden-1-ylidene)($\eta^5$-2-methyl-4,6-diisopropyl-1H-inden-1-ylidene)ethylstannyl]-7-($\eta^5$-cyclopenta-2,4-dien-1-ylidene)-7-($\eta^5$-1H-inden-1-ylidene)-3-oxa-4-silaheptane]dizirconium, tetrachloro[1-[($\eta^5$-2,7-dimethoxy-9H-fluoren-9-ylidene)($\eta^5$-1H-inden-1-ylidene)propylsilyl]-8-($\eta^5$-cyclopenta-2,4-dien-1-ylidene)-9-($\eta^5$-9H-fluoren-9-ylidene)-4-oxa-5-silanonane]dizirconium, tetrachloro(1-[bis($\eta^5$-7-methyl-5-phenyl-1H-inden-1-ylidene)-tert-butylsilyl]-5-($\eta^5$-1H-inden-1-ylidene)-5-($\eta^5$-4-ethyl-9H-fluoren-9-ylidene)-2-oxa-3-silapentane]dizirconium, tetrachloro[1-[($\eta^5$-cyclopenta-2,4-dien-1-ylidene)($\eta^5$-9H-fluoren-9-ylidene)methylsilyl]-7,7-bis($\eta^5$-2-methyl-4-naphthyl-1H-inden-1-ylidene)-3-oxa-4-silaoctane]dizirconium, tetrachloro[1-[bis($\eta^5$-1H-inden-1-ylidene)methylsilyl]-8-($\eta^5$-cyclopenta-2,4-dien-1-ylidene)-8-($\eta^5$-9H-fluoren-9-ylidene)-4,4-dimethyl-3,5-dioxa-4-silanonane]dizirconium, tetrachloro[1-[bis($\eta^5$-2-methyl-1H-inden-1-ylidene)methoxysilyl]-7-($\eta^5$-2,3,4,5-tetramethylcyclopenta-2,4-dien-1-ylidene)-7-($\eta^5$-9H-fluoren-9-ylidene)-3,5-dioxa-4-silaoctane]dizirconium, tetrachloro-[1-[bis($\eta^5$-2-methyl-4-phenyl-1H-inden-1-ylidene)phenylgermyl]-8-($\eta^5$-cyclopenta-2,4-dien-1-ylidene)-8-($\eta^5$-9H-fluoren-9-ylidene)-3,5-dioxa-4-silanonane]dizirconium, tetrachloro[1-[bis($\eta^5$-4-chloro-2-methyl-1H-inden-1-ylidene)ethylsilyl]-8,9-bis($\theta^5$-2,7-di-tert-butyl-9H-fluoren-9-ylidene)-4,6-dioxa-5-siladecane]dizirconium, tetrachloro[2,2-bis($\eta^5$-1H-inden-1-ylidene)-10-($\eta^5$-2-benzylcyclopenta-2,4-dien-1-ylidene)-10-($\eta^5$-4-methoxy-1H-inden-1-ylidene)-5,7-dioxa-6-siladecane]dizirconium, tetrachloro[1-[bis($\eta^5$-1H-inden-1-ylidene)methylstannyl]-9-($\eta^5$-cyclopenta-2,4-dien-1-ylidene)-9-($\eta^5$-9-fluoren-9-ylidene)-3,5-dioxa-4-siladecane]dizirconium, tetrachloro[1-[($\eta^5$-2-methyl-4-phenyl-1H-inden-1-ylidene)($\eta^5$-2-methyl-4,6-diisopropyl-1H-inden-1-ylidene)ethylstannyl]-7-($\eta^5$-cyclopenta-2,4-dien-1-ylidene)-7-($\eta^5$-1H-inden-1-ylidene)-4,6-dioxa-5-siladodecane]dizirconium, tetrachloro[1-[($\eta^5$-2,7-dimethoxy-9H-fluoren-9-ylidene)($\eta^5$-1H-inden-1-ylidene)propylsilyl]-8-($\eta^5$-cyclopenta-2,4-dien-1-ylidene)-9-($\eta^5$-9H-fluoren-9-ylidene)-3,5-dioxa-4-silanonane]dizirconium, tetrachloro[1-[bis($\eta^5$-7-methyl-5-phenyl-1H-inden-1-ylidene)-tert-butylsilyl]-5-($\eta^5$-1H-inden-1-ylidene)-5-($\eta^5$-4-ethyl-9H-fluoren-9-ylidene)-2,4-dioxa-3-silapentane]dizirconium, tetrachloro[1-[($\eta^5$-cyclopenta-2,4-dien-1-ylidene)($\eta^5$-9H-fluoren-9-ylidene)methylsilyl-9,9-bis($\eta^5$-2-methyl-4-naphthyl-1H-inden-1-ylidene)-3,5-dioxa-4-siladecane]dizirconium, tetrachloro[4-($\eta^5$-cyclopenta-2,4-dien-1-ylidene)-4-($\eta^5$-9H-fluoren-9-ylidene)-1,1-bis($\eta^5$-1H-inden-1-ylidene)silacyclohexane]dizirconium, tetrachloro[1,1-bis($\eta^5$-2-methyl-1H-inden-1-ylidene)-4-($\eta^5$-2,3,4,5-tetramethylcyclopenta-2,4-dien-1-ylidene)-4-($\eta^5$-9H-fluoren-9-ylidene)silacycloheptane]dizirconium, tetrachloro[1,1-bis($\eta^5$-2-methyl-4-phenyl-1H-inden-1-ylidene)-4-($\eta^5$-cyclopenta-2,4-dien-1-ylidene)-4-($\eta^5$-9H-fluoren-9-ylidene)silacyclohexane]dizirconium, tetrachloro(7,7-bis($\eta^5$-4-chloro-2-methyl-1H-inden-1-ylidene)-1,2-bis($\eta^5$-2,7-di-tert-butyl-9H-fluoren-9-ylidene)silacyclonon-4-ene]dizirconium, tetrachloro[1,1-bis($\eta^5$-1H-inden-1-ylidene)-5-($\eta^5$-2-benzylcyclopenta-2,4-dien-1-ylidene)-5-($\eta^5$-4-methoxy-1H-inden-1-ylidene)silacyclohexane]dizirconium, tetrachloro[1,1-bis($\eta^5$-1H-inden-1-ylidene)-7-($\eta^5$-cyclopenta-2,4-dien-1-ylidene)-7-($\eta^5$-9H-fluoren-9-ylidene)silacyclohexane]dizirconium, tetrachloro[1-($\eta^5$-2-methyl-4-phenyl-1H-inden-1-ylidene)-2-($\eta^5$-2-methyl-4,6-diisopropyl-1H-inden-1-ylidene)-6-($\eta^5$-cyclopenta-2,4-dien-1-ylidene)-6-($\eta^5$-1H-inden-1-ylidene)-4-phenyl-7-methoxy-1-silacyclodeca-4,8-dien]dizirconium, tetrachloro[1-($\eta^5$-2,7-dinethoxy-9H-fluoren-9-ylidene)-2-($\eta^5$-1H-inden-1-ylidene)-4-($\eta^5$-cyclopenta-2,4-dien-1-ylidene)-5-($\eta^5$-9H-fluoren-9-ylidene)cyclohexane]dizirconium, tetrachloro[1,1-bis($\eta^5$-7-methyl-5-phenyl-1H-inden-1-ylidene)-3-($\eta^5$-1H-inden-1-ylidene)-3-($\eta^5$-4-ethyl-H-fluoren-9-ylidene)-5-oxacycloheptane]dizirconium, tetrachloro[2-($\eta^5$-cyclopenta-2,4-dien-1-ylidene)-2-($\eta^5$-9H-fluoren-9-ylidene)-5,5-bis($\eta^5$-2-methyl-4-naphthyl-1H-inden-1-ylidene)-3,4-diethylcyclooctane]dizirconium, tetrachloro[1-[1,2-bis($\eta^5$-1H-inden-1-ylidene)-1,2,2-trimethyldisilane-1-yl]-3-($\eta^5$-cyclopentane-2,4-dien-1-ylidene)-4-($\eta^5$-9H-fluoren-9-ylidene)-3,4-dimethylpentane]dizirconium, tetrachloro[1-[1,2-bis($\eta^5$-2-methyl-1H-inden-1-ylidene)-1,2,2-trimethyldisilane-1-yl]-6-($\eta^5$-2,3,4,5-tetramethylcyclopenta-2,4-dien-1-ylidene)-7-($\eta^5$-9H-fluoren-9-ylidene)-6,7-dimethyloctane]dizirconium, tetrachloro[1-[1,2-bis($\eta^5$-2-methyl-4-phenyl-1H-inden-1-ylidene)-1,2,2-triphenyldigerman-1-yl]-3-($\eta^5$-cyclopenta-2,4-dien-1-ylidene)-4-($\eta^5$-9H-fluoren-9-ylidene)-3-methyl-4-phenylpentane]dizirconium, tetrachloro[1-(1,2-bis($\eta^5$-2,7-di-tert-butyl-9H-fluoren-9-ylidene)-1,2,2-trimethyldisilane-1-yl]-3,4-bis($\eta^5$-4-chloro-2-methyl-1H-inden-1-ylidene)-3,4-dimethylpentane]dizirconium, tetrachloro[1-[1-($\eta^5$-1H-inden-1-ylidene)-2-($\eta^5$-2-benzylcyclopenta-2,4-dien-1-ylidene)-1,2,2-trimethyldisilane-1-yl]-3-($\eta^5$-2-benzylcyclopenta-2,4-dien-1-ylidene)-4-($\eta^5$-4-methoxy-1H-inden-1-ylidene)-4,5-dimethylhexane]dizirconium, tetrachloro[2,3-bis($\eta^5$-1H-inden-1-ylidene)]-8-($\eta^5$-cyclopenta-2,4-dien-1-ylidene)-9-($\eta^5$-9H-fluoren-9-ylidene)-3,5,8-trimethyl-3-siladecane]dizirconium, tetrachloro[2-($\eta^5$-2-methyl-4-phenyl-1H-inden-1-ylidene)]-3-($\eta^5$-2-methyl-4,6-diisopropyl-1H-inden-1-ylidene)-8-($\eta^5$-cyclopenta-2,4-dien-1-ylidene)-9-($\eta^5$-inden-1-ylidene)-3,5,8-triphenyl-3-stannadecane]dizirconium, octachloro[2,10-bis[bis($\eta^5$-1H-inden-1-ylidene)methylsilyl]-6,14-bis[1-($\eta^5$-7-methyl-5-phenyl-1H-inden-1-ylidene)-1-($\eta^5$-9H-fluoren-9-ylidene)ethyl]pentadecane]tetrazirconium, octachloro[2-[bis($\eta^5$-2-methyl-4-naphthyl-1H-inden-1-ylidene)methylsilyl]-10-[bis($\eta^5$-cyclopenta-2,4-dien-1-ylidene)methylsilyl]-6,14-bis[1-($\eta^5$-cyclopenta-2,4-dien-1-ylidene)-1-($\eta^5$-9H-fluoren-9-ylidene)ethyl]pentadecane]tetrazirconium, octachloro[3-[bis($\eta^5$-2-methyl-4-naphthyl-1H-inden-1-ylidene)methylsilyl]-7-[bis($\eta^5$-cyclopenta-2,4-dien-1-ylidene)methylsilyl]-15-[1-($\eta^5$-cyclopenta-2,4-dien-1-ylidene)-1-($\eta^5$-9H-fluoren-9-ylidene)ethyl]octadecane]tetrazirconium, octachloro[3-[bis($\eta^5$-2-methyl-4-naphthyl-1H-inden-1-ylidene)methylsilyl]-7-[bis($\eta^5$-cyclopenta-2,4-dien-1-ylidene)methylsilyl]-15-[1-($\eta^5$-cyclopenta-2,4-dien-1-ylidene)-1-($\eta^5$-9H-fluoren-9-ylidene)ethyl]-5,12-dimethyl-8-phenoxy-16-(1-naphthyl)octadecane]tetrazirconium, octachloro[2-[bis($\eta^5$-2-methyl-4-naphthyl-1H-inden-1-ylidene)methylsilyl]-7-[bis($\eta^5$-cyclopenta-2,4-dien-1-ylidene)methylsilyl]-8-[bis($\eta^5$-2-methyl-4-phenyl-1H-inden-1-ylidene)phenylgermyl]-15-[1-($\eta^5$-cyclopenta-2,4-dien-1-ylidene)-1-($\eta^5$-9H-fluoren-9-ylidene)ethyl]-16-[bis($\eta^5$-2-methyl-4,6-diisopropyl-1H-inden-1-ylidene)methoxysilyl]octadecane]tetrazirconium, octachloro[2,2,8,8-tetrakis($\eta^5$-1H-inden-1-ylidene)-5,11-bis($\eta^5$-cyclopenta-2,4-dien-1-ylidene)-5,11-bis($\eta^5$-9H-fluoren-9-ylidene)-2,8-disiladodecane]tetrazirconium, octachloro[2,3,8,8-tetrakis($\eta^5$-1H-inden-1-ylidene)-5,11-bis($\eta^5$-cyclopenta-2,4-dien-1-ylidene)-5,12-bis($\eta^5$-9H-fluoren-9-ylidene)-2,8-disilatetradecane]tetrazirconium and octachloro[2,9-bis($\eta^5$-2-methyl-1H-inden-1-ylidene)-2,9-bis($\eta^5$-9H-fluoren-9-ylidene)-5,11-bis($\eta^5$-cyclopenta-2,4-dien-1-ylidene)-5,11-bis($\eta^5$-2,3,4,5-tetramethylcyclopenta-2,4-dien-1-ylidene)-2,9-disiladodecane]tetrazirconium.

12. A metallocene compound containing at least two metallocene fragments L—MX$_2$—L which contain the same metal atom and which are different from one another and having the formula I

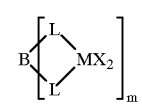

where B is

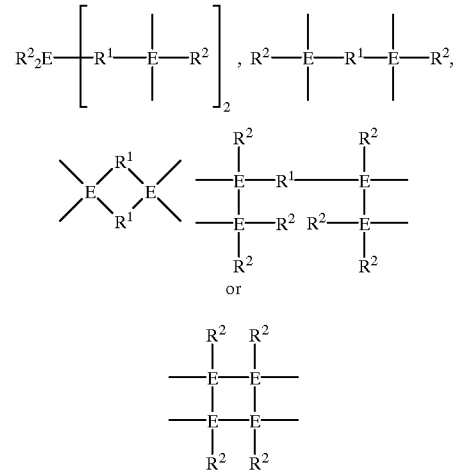

where the radicals $R^1$ are identical or different and are each a divalent $C_1$–$C_{40}$-hydrocarbon-containing bridging unit which can also contain one or more heteroatoms, the radicals $R^2$ are identical or different and are each a hydrogen atom, a halogen atom or a $C_1$–$C_{40}$-hydrocarbon-containing radical, and E are identical or different and are each, independently of one another, a carbon, silicon, germanium or tin atom, m is an integer from 2 to 100,000, M is a metal atom of group IVb, Vb or VIb, of the Periodic Table of the Elements, X are identical or different in one metallocene fragment L—MX$_2$—L and are each, independently of one another, hydrogen, a C$_1$–C$_{40}$-hydrocarbon-containing group, an OH group, a halogen atom or a pseudo-halogen, L are identical or different in one metallocene fragment L—MX$_2$—L and are each, independently of one another, a π ligand or another electron donor.

* * * * *

UNITED STATES PATENT AND TRADEMARK OFFICE
CERTIFICATE OF CORRECTION

PATENT NO. : 6,262,197 B1
DATED : July 17, 2001
INVENTOR(S) : Aulbach et al.

It is certified that error appears in the above-identified patent and that said Letters Patent is hereby corrected as shown below:

Column 17,
Line 50, please delete "are each".
Line 53, "arylalkyl" should read as -- arylalkyl group --.

Column 18,
Line 3, "butylcylopentadienylidene," should read as -- butylcyclopentadienylidene --.

Column 20,
Line 13, "tetrachloro(1-[bis($\eta^5$-7-...." should read as -- tetrachloro[1-[bis($\eta^5$-7-.... --.
Line 33, "...-bis($\theta^5$-2,7-di-tert-..." should read as -- -bis($\eta^5$-2,7-di-tert-... --.

Column 21,
Line 16, "...($\eta^5$-2,7-dinethoxy-9H-..." should read as -- ...($\eta^5$-2,7-dimethoxy-9H-... --.
Line 27, "trimethyldisilane-1-yl]..." should read as -- trimethyldisilan-l-yl]... --.
Line 31, "2,2-trimethyldisilane-l-yl]..." should read as -- 2,2-triethyldisilan-l-yl]... --.
Line 39, "ylidene)-1,2,2,-trimethyldisilane-l-yl]..." should read as -- "ylidene)-1,2,2,-trimethyldisilan-l-yl]... --.
Line 44, trimethyldisilane-l-yl]..." should read as -- trimethyldisilan-l-yl]... --.
Line 52, "...-9-$\eta^5$-inden-l-" should read as -- ...-9-$\eta^5$-1H inden-l- --.

Signed and Sealed this

Second Day of July, 2002

*Attest:*

*Attesting Officer*

JAMES E. ROGAN
*Director of the United States Patent and Trademark Office*